(12) United States Patent
Critz et al.

(10) Patent No.: US 6,416,524 B1
(45) Date of Patent: Jul. 9, 2002

(54) DOUBLE SCALPEL

(76) Inventors: Carl H. Critz, 24 Tea Treet Ct., Danville, CA (US) 94526; Joseph Hale, 14 Mayo Dr., Warren, RI (US) 02885

( * ) Notice: Subject to any disclaimer, the term of this patent is extended or adjusted under 35 U.S.C. 154(b) by 0 days.

(21) Appl. No.: 09/826,150

(22) Filed: Apr. 5, 2001

(51) Int. Cl.⁷ .................................................. A61B 17/32
(52) U.S. Cl. ........................................ 606/167; 30/315
(58) Field of Search ............................ 606/1, 166, 167; 30/315, 299, 312, 340

(56) References Cited

U.S. PATENT DOCUMENTS

| | | |
|---|---|---|
| 1,665,064 A | 4/1928 | Magrath |
| 1,697,091 A | 1/1929 | Skubic |
| 2,448,383 A | 8/1948 | Mathaus |
| 3,452,754 A | 7/1969 | Stayer |
| 3,998,229 A | 12/1976 | Barton |
| 4,969,267 A | 11/1990 | Anenberg |
| 5,026,385 A | 6/1991 | Schutte et al. |
| 5,100,391 A | 3/1992 | Schutte et al. |
| 5,447,516 A | 9/1995 | Gardner |
| 5,951,580 A | 9/1999 | Ashraf |

FOREIGN PATENT DOCUMENTS

DE        2320380    * 11/1974   .................. 606/167

* cited by examiner

Primary Examiner—Henry J. Recla
Assistant Examiner—William W. Lewis
(74) Attorney, Agent, or Firm—John P. McGonagle

(57) ABSTRACT

A plurality of scalpel handles, one master handle and one or more slave handles. The master handle and one of the slave handles are interconnected to provide uniform, parallel blade separation of two scalpels and their blades.

3 Claims, 2 Drawing Sheets

DOUBLE SCALPEL

BACKGROUND OF THE INVENTION

This invention relates general to scalpels, and in particular to means for interconnecting two scalpels to form a double scalpel for accurate sectioning of soft or unfixed tissue for histology processing.

When soft tissues are prosected, the first cut is generally wavy and the second generally cut distorts the tissues resulting in tissue sections that are too thick, too thin, or uneven or non-uniform in thickness. For this reason, many pathologists fix large or soft specimens over night in order to have firmer specimens to prosect and produce thinner, more uniform sections 2 to 4 mm in thickness. This permits better infiltration and dehydration. Although fixation is delayed in intact large specimens compared to adequately thin sections cut fresh and placed in fixative, because fixation is time and thickness dependent.

SUMMARY OF THE INVENTION

The present invention allows cutting of uniform thickness sections in soft tissues such as the bowel, brain, spleen, and lung, in the fresh state thereby reducing turn around time and providing better fixation for better histology. The present invention accomplishes this by providing a number of blade handles, one master handle and one or more slave handles. The master handle and one of the slave handles are interconnected in parallel to provide uniform, parallel blade separation of two blades. In another embodiment of the invention the separation between blades is adjustable.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF THE INVENTION

Figure 1:
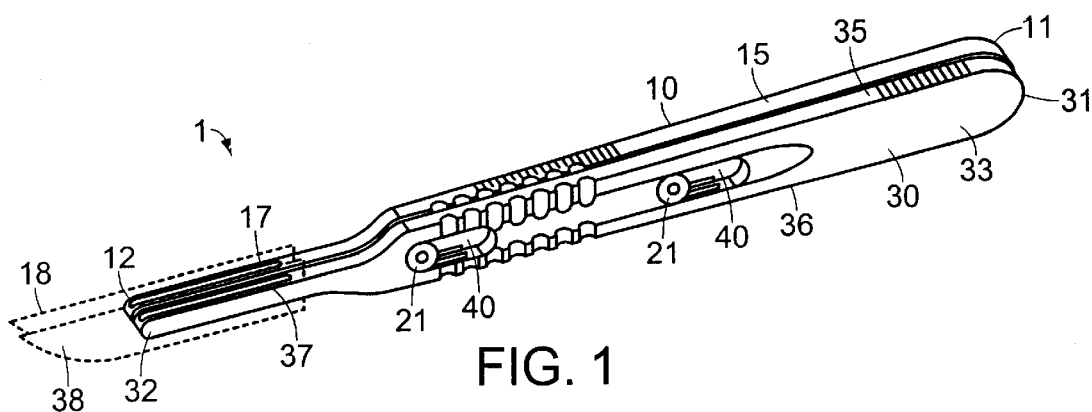
FIG. 1 is a side perspective view of one interconnected embodiment of the invention.
Figure 2:
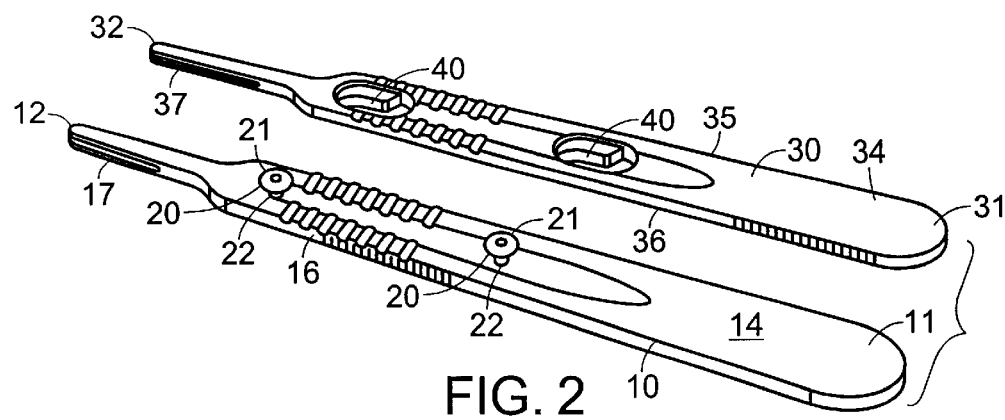
FIG. 2 is a side perspective view of the two disconnected handles of FIG. 1 with facing sides in view.
Figure 3:
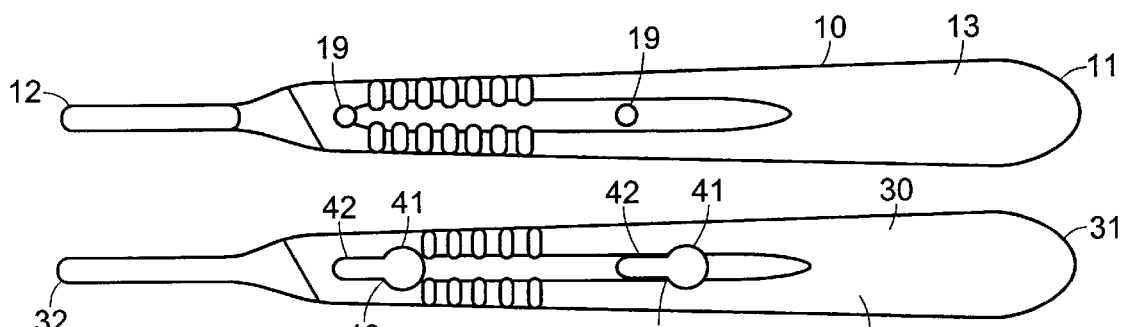
FIG. 3 is a side perspective view of the two disconnected handles of FIG. 1 with non-facing sides in view.
Figure 4:
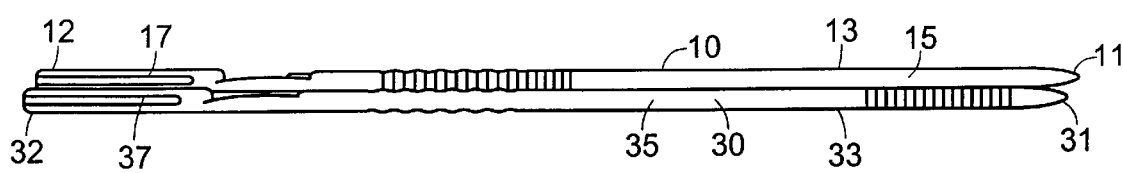
FIG. 4 is a top view of the embodiment illustrated in FIG. 1.
Figure 5:
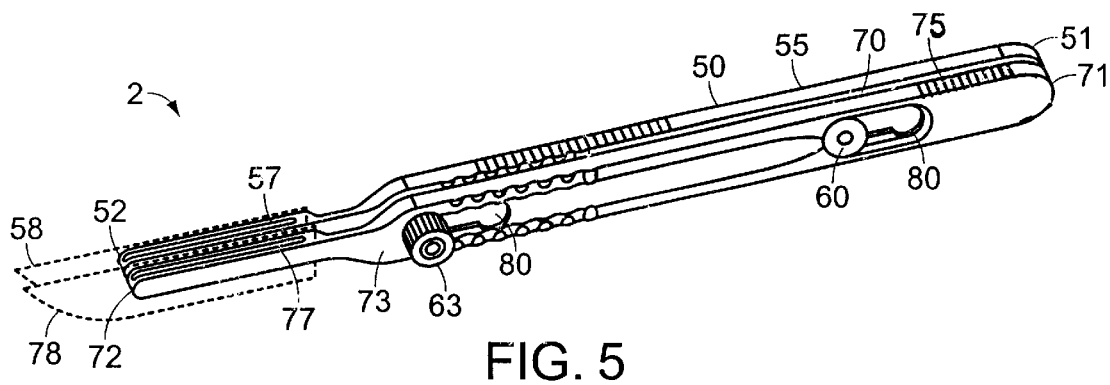
FIG. 5 is a side perspective view of another interconnected embodiment of the invention.
Figure 6:
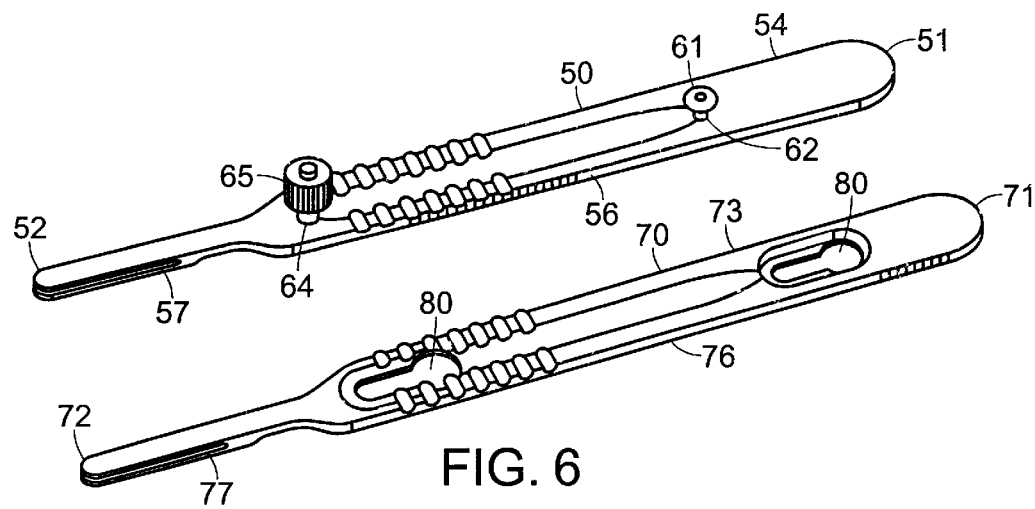
FIG. 6 is a side perspective view of the two disconnected handles of FIG. 5 with facing sides in view.
Figure 7:
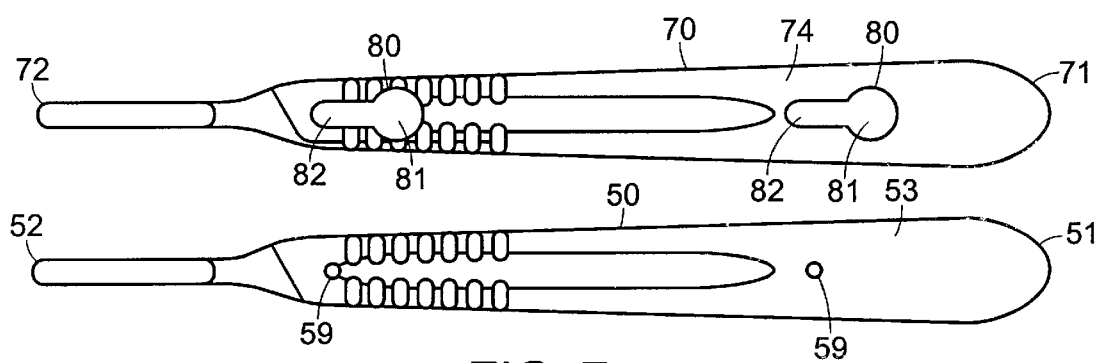
FIG. 7 is a side perspective view of the two disconnected handles of FIG. 5 with non-facing sides in view.
Figure 8:
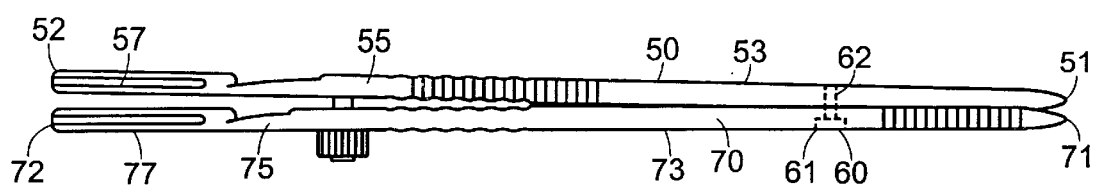
FIG. 8 is a top view of the embodiment illustrated in FIG. 5.

Referring to the drawings in detail wherein like elements are indicated by like numerals, there are shown in FIGS. 1–4, and FIGS. 5–8, double scalpel embodiments 1, 2 constructed according to the principles of the present invention.

Referring more particularly to FIGS. 1–4, the double scalpel 1 shown in these figures is comprised of a "master" scalpel handle 10 and a separate "slave" scalpel handle 30. The master scalpel handle 10 has a rounded proximal end 11, a distal end 12, an "outside" surface 13, an "inside" surface 14, a top edge 15 and a bottom edge 16, said proximal end 11 and distal end 12 defining the longitudinal axis of the scalpel handle 10. The master scalpel distal end 12 has a slot 17 formed therein, said slot 17 being adapted to hold a scalpel blade 18. The master scalpel inside surface 14 has two rounded, threaded apertures 19 formed therein, said apertures 19 being formed centrally along the longitudinal axis of the master scalpel handle 10. The master handle 10 has two pegs 20. Each peg 20 has a cap 21 and a threaded body 22. Each peg body 22 threadingly engages an aperture 19 wherein each peg cap 21 is positioned a selected distance from the handle inside surface 14.

The slave scalpel handle 30 has a rounded proximal end 31, a distal end 32, an "outside" surface 33, an "inside" surface 34, a top edge 35 and a bottom edge 36, said proximal end 31 and distal end 32 defining the longitudinal axis of the slave scalpel handle 30. The slave scalpel handle distal end 32 has a slot 37 formed therein, said slot 37 being adapted to hold a scalpel blade 38. The slave scalpel inside surface 34 has two key hole slots 40 formed therein, said key hole slots 40 being formed centrally along the longitudinal axis of the slave scalpel handle 30. Each key hole slot 40 is comprised of a rounded rearward aperture 41 and a forward narrow channel 42, said rearward aperture 41 being positioned toward the handle proximal end 31 and said channel 42 being positioned toward the handle distal end 31, said rearward aperture 41 and a forward narrow channel 42 defining a key hole slot longitudinal axis, said key hole slot longitudinal axis being coincident with the slave handle longitudinal axis, both aperture 41 and channel 42 opening through the scalpel handle 30 to and through the scalpel handle outside surface 33.

The master scalpel handle 10 and slave scalpel handle 30 are adapted to being joined together by positioning the master scalpel handle inside surface 14 along side the slave scalpel handle inside surface 34, insertion of the master scalpel handle peg caps 21 into and through the slave scalpel handle key hole rounded apertures 41, and sliding the master handle 10 forward so that the peg bodies 22 engage the key hole channels 42.

Referring more particularly to FIGS. 5–8, wherein an alternate embodiment of the invention is shown, the double scalpel 2 shown in these figures is comprised of a "master" scalpel handle 50 and a separate "slave" scalpel handle 70. The master scalpel handle 50 has a rounded proximal end 51, a distal end 52, an "outside" surface 53, an "inside" surface 54, a top edge 55 and a bottom edge 56, said proximal end 51 and distal end 52 defining the longitudinal axis of the scalpel handle 50. The master scalpel distal end 52 has a slot 57 formed therein, said slot 57 being adapted to hold a scalpel blade 58. The master scalpel inside surface 54 has two rounded, threaded apertures 59 formed therein, said apertures 59 being formed centrally along the longitudinal axis of the master scalpel handle 50, one aperture 59 rearward toward the proximal handle end 51 and the other aperture forward toward the distal handle end 52. The master handle 50 has a rearward peg 60, said peg 60 having a cap 61 and a threaded body 62, said peg body 22 threadingly engaging said rearward aperture 59 wherein said peg cap 61 is positioned a selected distance from the handle inside surface 54. The master handle 50 also has a forward adjustable peg 63, said peg 63 having a threaded body 64 and a knurled nut 65 threadingly engaging said threaded body 64, said peg body 64 also threadingly engaging said forward aperture 59 wherein said peg nut 65 is positioned a selected distance from the handle inside surface 54.

The slave scalpel handle 70 has a rounded proximal end 71, a distal end 72, an "outside" surface 73, an "inside" surface 74, a top edge 75 and a bottom edge 76, said proximal end 71 and distal end 72 defining the longitudinal axis of the slave scalpel handle 70. The slave scalpel handle distal end 72 has a slot 77 formed therein, said slot 77 being adapted to hold a scalpel blade 78. The slave scalpel inside surface 74 has two key hole slots 80 formed therein, said key hole slots 80 being formed centrally along the longitudinal axis of the slave scalpel handle 70. Each key hole slot 80 is comprised of a rounded rearward aperture 81 and a forward narrow channel 82, said rearward aperture 81 being positioned toward the handle proximal end 71 and said channel 82 being positioned toward the handle distal end 71, said rearward aperture 81 and a forward narrow channel 82 defining a key hole slot longitudinal axis, said key hole slot longitudinal axis being coincident with the slave handle longitudinal axis, both aperture 81 and channel 82 opening through the scalpel handle 70 to and through the scalpel handle outside surface 73.

The master scalpel handle 50 and slave scalpel handle 70 are adapted to being joined together by positioning the master scalpel handle inside surface 54 along side the slave scalpel handle inside surface 74, insertion of the master scalpel handle peg cap 61 and nut 65 into and through the slave scalpel handle key hole rounded apertures 81, and sliding the master handle 50 forward so that the peg bodies 62, 64 engage the key hole channels 82.

The adjustable peg knurled nut 65 of the second invention embodiment 2 allows a user to adjust the separation between master scalpel blade 58 and slave scalpel blade 78, wherein the first invention embodiment 1 has a preset separation between master blade 18 and slave scalpel blade 38.

It is understood that the above-described embodiments are merely illustrative of the application. Other embodiments may be readily devised by those skilled in the art which will embody the principles of the invention and fall within the spirit and scope thereof.

We claim:

1. A double scalpel assembly, comprising:

a master scalpel having a handle and a blade, said master scalpel handle having a rounded proximal end, a distal end, an outside surface, an inside surface, a top edge and a bottom edge, said proximal end and distal end defining a scalpel handle longitudinal axis, said master scalpel distal end having a slot formed therein, said slot adapted to hold a scalpel blade, said master scalpel inside surface having two rounded, threaded apertures formed therein, said apertures being formed centrally along the longitudinal axis of the master scalpel handle, said master scalpel handle has a plurality of pegs, each peg having a cap and a body, each peg body fixedly engaging one of said apertures, wherein each peg cap is positioned a selected distance from the master handle inside surface;

a slave scalpel having a handle and a blade, said slave scalpel being interconnected to said master scalpel thereby providing uniform, parallel blade separation of two blades, said slave scalpel handle having a rounded proximal end, a distal end, an outside surface, an inside surface, a top edge and a bottom edge, said proximal end and distal end defining a longitudinal axis of the slave scalpel handle, said slave scalpel handle distal end having a slot formed therein, said slot being adapted to hold a scalpel blade, said slave scalpel inside surface having a plurality of key hole slots formed therein, said key hole slots being formed centrally along the longitudinal axis of the slave scalpel handle, each key hole slot being comprised of a rounded rearward aperture and a forward narrow channel, said rearward aperture being positioned toward the handle proximal end and said forward channel being positioned toward the handle distal end, a rearward aperture and a forward narrow channel defining a key hole slot longitudinal axis, said key hole slot longitudinal axis being coincident with the slave handle longitudinal axis, both aperture and channel opening through the scalpel handle to and through the scalpel handle outside surface.

2. A scalpel assembly as recited in claim 1, wherein:

said master scalpel handle and slave scalpel handle are adapted to being joined together by positioning the master scalpel handle inside surface along side the slave scalpel handle inside surface, insertion of the master scalpel handle peg caps into and through the slave scalpel handle key hole rounded apertures, and sliding the master handle forward so that the peg bodies engage the key hole channels.

3. A scalpel assembly as recited in claim 2, further comprising:

the peg closest to the master handle has a threaded body and a cap comprised of a knurled nut threadingly engaging said threaded body.

* * * * *